United States Patent
Tschantz et al.

(10) Patent No.: US 10,039,851 B2
(45) Date of Patent: Aug. 7, 2018

(54) WAX MELT SYSTEM

(71) Applicant: S.C. Johnson & Son, Inc., Racine, WI (US)

(72) Inventors: Sandra D. Tschantz, Kenosha, WI (US); James T. Walker, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 306 days.

(21) Appl. No.: 14/166,185

(22) Filed: Jan. 28, 2014

(65) Prior Publication Data

US 2015/0209463 A1    Jul. 30, 2015

(51) Int. Cl.
| | |
|---|---|
| *A61L 9/012* | (2006.01) |
| *B65D 25/04* | (2006.01) |
| *C11C 5/00* | (2006.01) |
| *C11C 5/02* | (2006.01) |

(52) U.S. Cl.
CPC .............. *A61L 9/012* (2013.01); *B65D 25/04* (2013.01); *C11C 5/002* (2013.01); *C11C 5/008* (2013.01); *C11C 5/023* (2013.01)

(58) Field of Classification Search
CPC . C11C 5/00; C11C 5/008; C11C 5/021; C11C 5/023; B65D 25/04
See application file for complete search history.

(56) References Cited

U.S. PATENT DOCUMENTS

| | | | | |
|---|---|---|---|---|
| 2,804,205 | A | * | 8/1957 | Barton ............. B65D 65/42 206/447 |
| 4,759,699 | A | * | 7/1988 | Rubarth ............ F21V 35/00 431/291 |
| D320,994 | S | * | 10/1991 | Kafka ..................... D15/90 |
| 5,578,089 | A | | 11/1996 | Elmastoy |
| 5,959,129 | A | | 9/1999 | Van Dam |
| 6,019,804 | A | | 2/2000 | Requejo |
| 6,063,144 | A | | 5/2000 | Caldaza |
| 6,106,597 | A | | 8/2000 | Starks |
| 6,214,918 | B1 | | 4/2001 | Johnson |
| 6,224,641 | B1 | | 5/2001 | Matzat |
| 6,284,007 | B1 | | 9/2001 | Tao |
| 6,380,462 | B1 | | 4/2002 | Kridl |
| 6,497,735 | B2 | | 12/2002 | Tao |
| 6,503,285 | B1 | | 1/2003 | Murphy |
| 6,599,334 | B1 | | 7/2003 | Anderson |
| 6,634,513 | B1 | * | 10/2003 | Hardy .............. A47B 87/007 211/194 |
| 6,645,261 | B2 | | 11/2003 | Murphy |
| 6,730,137 | B2 | | 5/2004 | Pesu |
| 6,758,869 | B2 | | 7/2004 | Roeske |
| 6,770,104 | B2 | | 8/2004 | Murphy |

(Continued)

OTHER PUBLICATIONS

Clamshell package for wax melts—dated Aug. 10, 2008.*

(Continued)

*Primary Examiner* — Nathaniel Herzfeld
(74) *Attorney, Agent, or Firm* — Quarles & Brady LLP

(57) ABSTRACT

A wickless wax melt includes a prilled wax body defined by two opposing substantially planar surfaces and four sidewalls. At least one volatile material is disposed within the wax body and the wax body is characterized by an oil content up to about 10% to impart a non-greasy feel thereto and wherein the wax body weighs more than about 0.01 kg.

9 Claims, 19 Drawing Sheets

(56) References Cited

U.S. PATENT DOCUMENTS

| | | | |
|---|---|---|---|
| 6,773,469 B2 | 8/2004 | Murphy | |
| 6,776,808 B2 | 8/2004 | Foster | |
| 6,797,020 B2 | 9/2004 | Murphy | |
| 6,824,572 B2 | 11/2004 | Murphy | |
| 6,852,140 B1 | 2/2005 | Roeske | |
| 7,018,432 B2 | 3/2006 | Moussouni | |
| 7,067,772 B2 * | 6/2006 | Tanner | A61L 9/03 219/443.1 |
| 7,128,766 B2 | 10/2006 | Murphy | |
| 7,160,337 B2 | 1/2007 | Williams | |
| 7,192,457 B2 | 3/2007 | Murphy | |
| 7,217,301 B2 | 5/2007 | Murphy | |
| 7,220,288 B2 | 5/2007 | D'Amico | |
| 7,387,649 B2 | 6/2008 | Tao | |
| 7,420,008 B2 | 9/2008 | Bloom | |
| 7,462,205 B2 | 12/2008 | Murphy | |
| 7,510,584 B2 | 3/2009 | Cap | |
| 7,569,084 B2 | 8/2009 | Tao | |
| 7,588,607 B1 | 9/2009 | Cap | |
| 7,713,314 B2 | 5/2010 | Jones | |
| 7,731,767 B2 | 6/2010 | Tao | |
| 7,959,689 B2 * | 6/2011 | Cagle | C11C 5/002 431/288 |
| 8,021,443 B2 | 9/2011 | Cagle | |
| 8,070,833 B2 | 12/2011 | Murphy | |
| 8,070,834 B2 | 12/2011 | Tao | |
| D748,499 S * | 2/2016 | Hanna | D9/425 |
| 2003/0134244 A1 * | 7/2003 | Gray | C11C 5/021 431/288 |
| 2006/0218862 A1 * | 10/2006 | Dyas | A01G 9/104 47/86 |
| 2006/0240371 A1 * | 10/2006 | Palmer | F21V 35/00 431/289 |
| 2007/0282000 A1 | 12/2007 | Murphy | |
| 2008/0138753 A1 | 6/2008 | Tao | |
| 2008/0282601 A1 | 11/2008 | Luttke | |
| 2009/0217568 A1 | 9/2009 | Murphy | |
| 2010/0024281 A1 | 2/2010 | Lemke | |
| 2010/0044924 A1 | 2/2010 | Cap | |
| 2010/0205851 A1 | 8/2010 | Uptain | |
| 2010/0251671 A1 | 10/2010 | Thompson et al. | |
| 2014/0374415 A1 * | 12/2014 | Propes | B65D 1/36 220/23.8 |

OTHER PUBLICATIONS

Look-whos—dated Nov. 8, 2012.*
Candle Molds, Sep. 11, 2010.*
BitterCreekSouth, Oct. 20, 2011.*
Ivanovsky, Tiffany: "Make Your Own Scented Wax Cubes" {DIY Tutorial}, Retrieved from the Internet: URL:http://mylitter.com/media/how-to-make-your-own-scented-wax/ [retrieved Mar. 26, 2015] Posted Sep. 27, 2013.
Anon: Peak Candle Supplies—"How to Make Wax Melts, Tarts, or Cubes", Retrieved from the Internet: URL:http://www.candletech.com/fragrant-living/make-wax-melt-tart-cubes/ [retrieved Apr. 9, 2015] Posted Jan. 3, 2014.
PCT/US2015/012873 International Search Report and Written Opinion dated Apr. 17, 2015.

* cited by examiner

WAX MELT SYSTEM

CROSS REFERENCE TO RELATED APPLICATIONS

Not applicable.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

The present disclosure relates generally to a wax melt system, and more particularly, to a wax melt system including a plurality of wax melts provided in a container having discrete receptacles to facilitate removal therefrom.

2. Description of the Background of the Invention

Candles have been used for centuries to provide illumination for the surrounding area. In more recent years, candles have been used as a fragrancing and/or deodorizing mechanism for the home. A typical candle includes a wax body with a wick extending therethrough. These types of candles are designed to burn when a flame is provided to the wick. When the wick is lit, the heat generated by the flame melts the wax body, which releases fragrance particles entrained therein. To continue releasing fragrance, the candle must remain lit. In many instances, consumers light the candle and continue moving about the household, oftentimes leaving the candle unattended.

Unfortunately, the use of candles with wicks may present a fire hazard. Consumers may forget that the candle is burning and leave the candle unattended for extended periods of time, which may cause a fire if molten wax and/or a portion of the flame splatters from the candle due to flashover or other problems associated with certain types of candles. In addition, the use of a candle with a wick for fragrance release incorporates the unpleasant smell of combustion into the fragrance profile, which is most evident when the candle is first lit and when extinguished.

In recent years, attempts have been made to provide a wickless candle solution that minimizes the fire hazard associated with candles, while at the same time provides the fragrancing benefits associated therewith. In one instance, typical wickless candle solutions include an electric warmer and a plurality of wax beads designed to be heated therein. The wax beads are usually provided in a container or bag that requires the consumer to tilt and/or pour the wax beads into the warmer. The wax beads are frequently very small and may be susceptible to spilling during this process. Further, consumers frequently must purchase a significant quantity of wax beads to provide the same fragrancing benefits as a traditional candle due to the smaller size of the beads.

In other instances, a typical wickless candle solution includes an electric warmer and one or more wax melts. The wax melts are usually provided in block form due to the manufacturing process utilized. In particular, the wax is poured into compartments of a container until the container is full. As the wax cools, a thin sheet of wax covers the individual wax melts to form a block of wax, e.g., in the shape of a conventional candy bar. During use, the consumer is required to break off or otherwise remove only a portion of the block of wax to use in the warmer. In these instances, some of the wax crumbles and chunks of wax may be inadvertently dislodged from the block. Further, the consumer is required to either handle the wax, which is frequently greasy to the touch, or is required to deform the container to push a portion of the wax block onto the warmer.

Therefore, a need exists for a wax melt system that overcomes one or more of the aforementioned problems. In particular, it would be desirable to provide a wax melt system that is non-greasy to the touch and is manufactured and provided in such a way that simplifies the steps that are required to remove the wax melts from the packaging. It would be further desirable to provide a wickless wax melt system that provides a more pure fragrance experience without the by-product odor from the combustion of the wick.

SUMMARY OF THE INVENTION

According to one aspect, a wickless wax melt includes a prilled wax body defined by two opposing substantially planar surfaces and four sidewalls. At least one volatile material is disposed within the wax body and the wax body is characterized by an oil content up to about 10% to impart a non-greasy feel thereto and wherein the wax body weighs more than about 0.01 kg.

According to another aspect, a package for wax melts includes a first and a second wickless wax melt, each having opposing substantially planar surfaces. A container has discrete receptacles for holding the first and second wax melts therein, wherein the first wax melt is held within a first receptacle and the second wax melt is held within a second receptacle.

According to a further aspect, a method of instructing the use of a wax melt system includes the step of providing instructions. The instructions include the step of directing a user to open a container having discrete receptacles with a wickless wax melt disposed in each receptacle. The instructions also include the step of directing a user to remove at least one wax melt from the container without contacting any other wax melt or portion thereof. Further, the instructions include the steps of directing a user to place the at least one wax melt onto a reservoir of a wax warmer and to supply power to the wax warmer.

DETAILED DESCRIPTION

Figure 1:
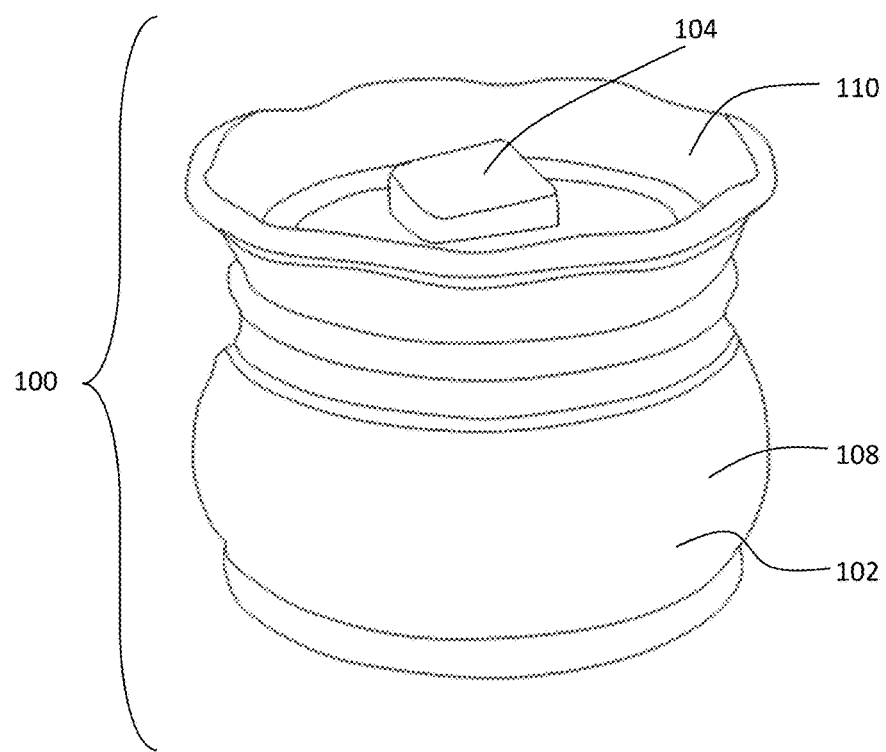
FIG. 1 is an isometric view of a wax melt system having a wax warmer and a wax melt according to a first embodiment.
Figure 2:
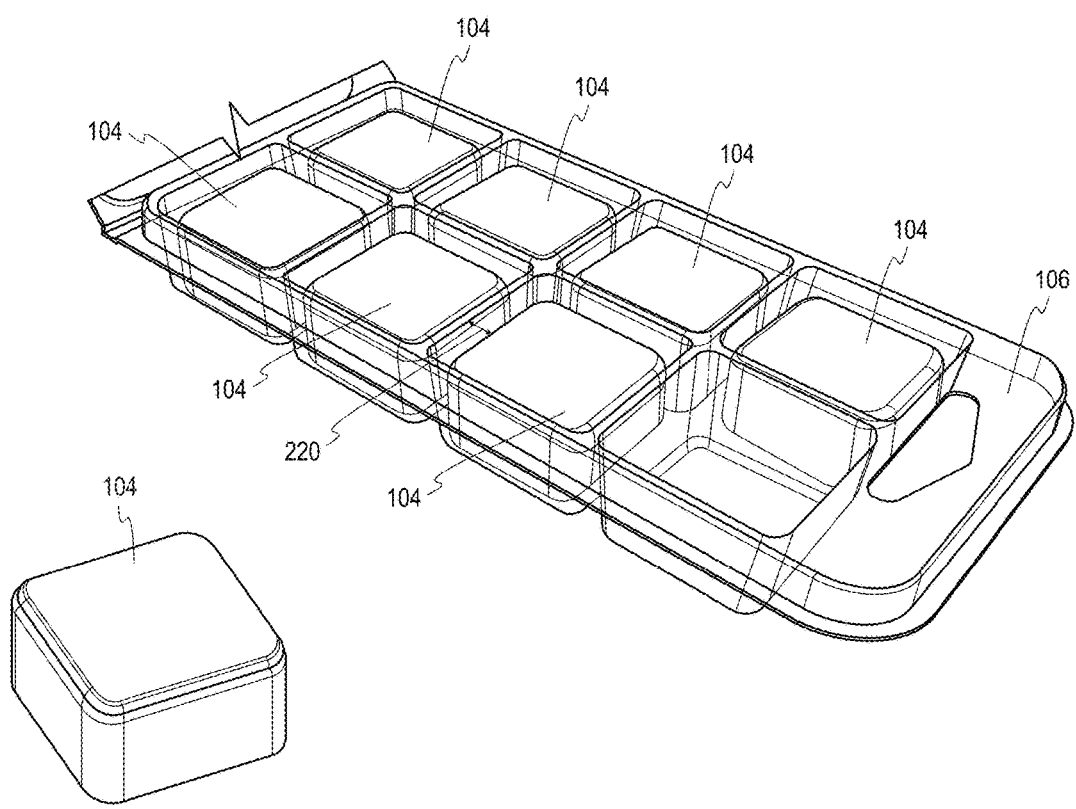
FIG. 2 is an isometric view of a plurality of wax melts disposed within and adjacent to a container.

With reference to FIGS. 1 and 2, one particular embodiment of a wax melt system 100 is illustrated that generally includes a wax warmer 102 designed to accommodate one or more wax melts 104. The wax melts 104 are provided in a container 106 (see FIG. 2) having particularly suitable characteristics with respect to storing, retaining, and removing the wax melts 104, as described in more detail below. One or more components of the wax melt system 100 may be sold separately or as part of a kit. The kit may include any of the components described herein and may further include instructions for use of the wax melt system 100. It is envisioned that the wax melt system 100 described herein includes at least one wax melt 104 that is devoid of a wick (e.g., wickless). Additionally, it is envisioned that the melting process of the wax melt 104 is accomplished via means that does not include a flame directly adjacent thereto. For example, in one embodiment, heat is applied to the wax melt 104 using a heater. In another embodiment, heat provided from a flame may be applied to the wax melt 104, but in this instance the flame does not contact the wax melt 104 directly and may be present within the wax warmer 102.

As shown in FIG. 1, the wax warmer 102 generally includes a body 108, a reservoir 110, and a heater assembly (not shown) disposed therein. The body 104 is designed to act as a support structure for the reservoir 110 and enclose internal components thereof (e.g., the heater assembly). The wax warmer 102 includes a power source (not shown) that is provided in the form of an electrical power cord, a battery, a tealight, and/or another power source that provides energy thereto. The wax warmer 102 may be characterized by any structure that provides a surface designed to transfer heat from the wax warmer 102 to the wax melt 104. One suitable wax warmer 102 is that disclosed in U.S. patent application Ser. No. 14/136,201, filed on Dec. 20, 2013, hereby incorporated by reference in its entirety.

Figure 3:
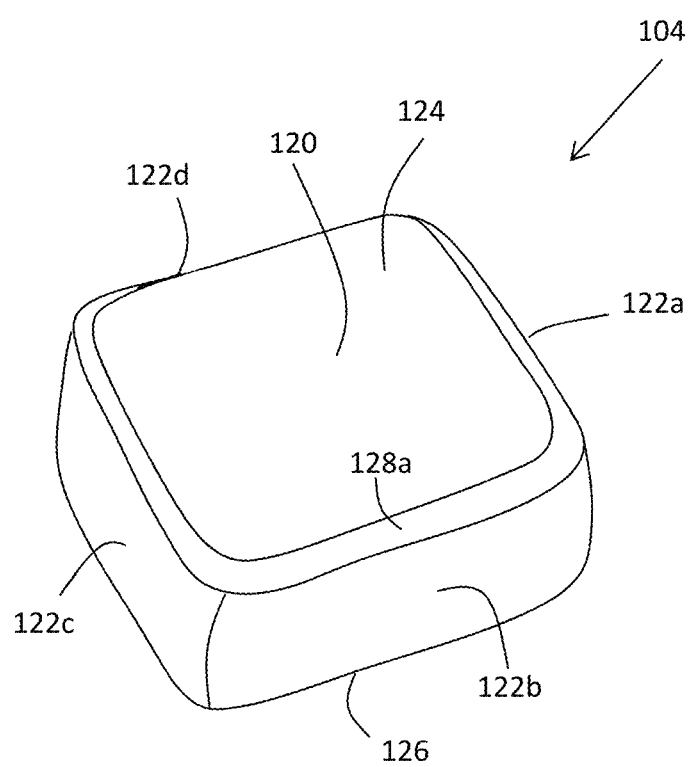
FIG. 3 is an isometric view of the wax melt of FIG. 2.
Figure 4:
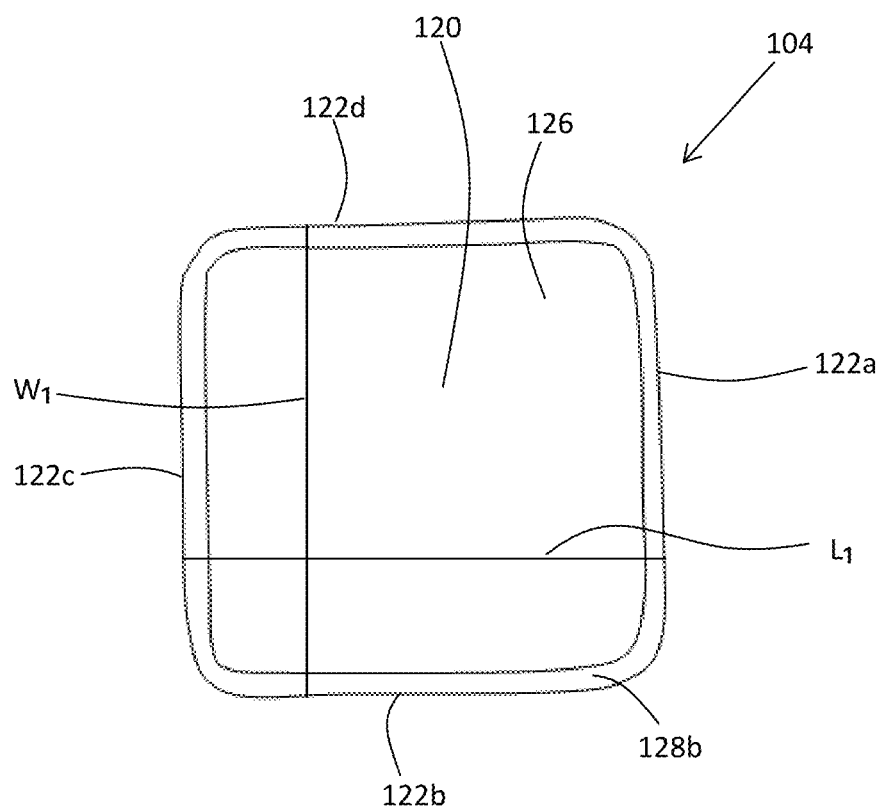
FIG. 4 is bottom elevational view of the wax melt of FIG. 2.
Figure 5:
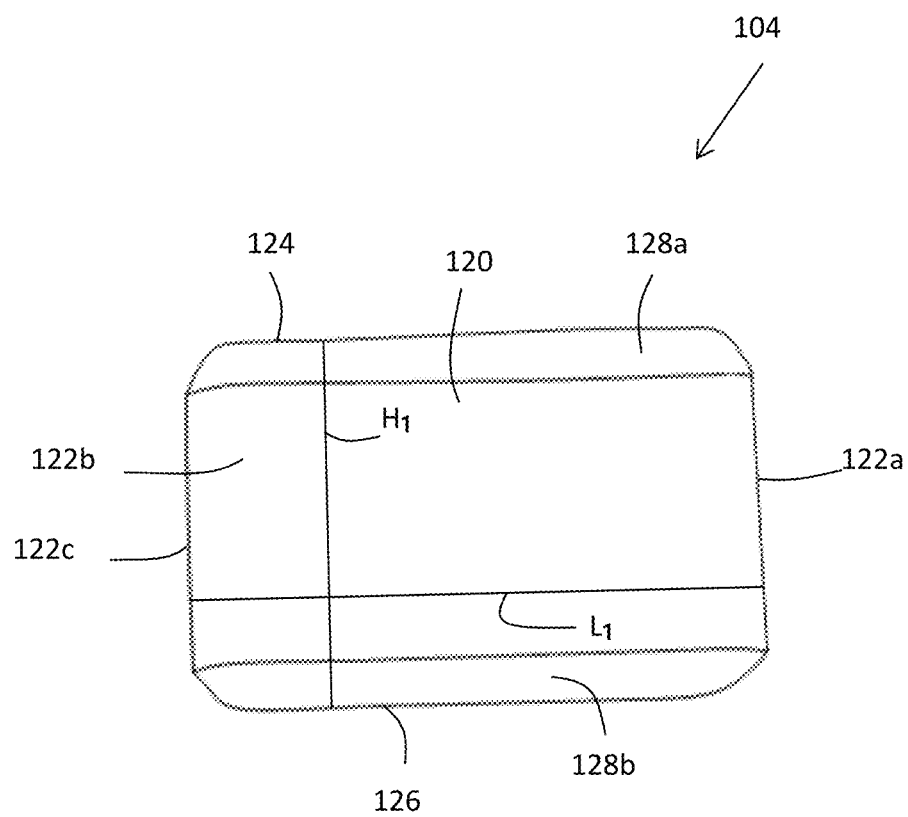
FIG. 5 is a side elevational view of the wax melt of FIG. 2.

As best seen in FIGS. 3-5, each wax melt 104 includes a wax body 120 defined by four sidewalls 122a-122d and opposing upper and lower surfaces 124, 126. The wax body 120 may have a generally square shape with a slightly rounded curvature imparted thereto at an area where the sidewalls 122a-122d intersect with each other, when viewed from above or below (see, e.g., FIG. 4). In one embodiment, each of the sidewalls 122a-122d and upper and lower surfaces 124, 126 are substantially planar in that there are no substantial surface interruptions beyond minor surface irregularities formed during the manufacturing process, such as those discussed below. In a further embodiment, the upper and/or lower surface 124, 126 may be imparted with one or more surface interruptions formed by embossing for decorative purposes. In all embodiments, the wax melt 104 does not include a surface interruption provided for the purpose of holding and/or surrounding a wick and/or a wick holder (not shown). In further embodiments, the sidewall(s) 122a-122d of the wax melt 104 may be provided in circular, triangular, or other shapes as opposed to square, whereby the wax melt 104 includes substantially flat upper and lower surfaces 124, 126.

As best seen in FIG. 5, upper and lower grooves 128a, 128b correspond to and circumscribe the upper and lower surfaces 124, 126, respectively, of the wax body 120. In particular, the grooves 128a, 128b are disposed at the intersection of the upper and lower surfaces 124, 126 and the sidewalls 122a-122d. The grooves 128a, 128b are formed during the manufacturing process, which is described in more detail below. In the embodiment depicted, the grooves 128a, 128b each extend around the entire periphery of the wax body 120. In other embodiments, the grooves 128a, 128b may be absent, at least partially interrupted, or extend only around a portion of the body 120.

To properly fit into the warmer 102 and to ensure proper melting characteristics, the wax melts 104 are preferably shaped to a specific dimension that corresponds with the dimensions of the warmer 102. In one embodiment, each wax melt 104 includes a height dimension $H_1$ (see FIG. 5) as measured along the sidewall 122a-122d from the upper surface 124 to the lower surface 126. In one embodiment, the height $H_1$ dimension is between about 10 mm to about 30 mm, and in another embodiment is between about 15 mm to about 20 mm. In another embodiment, the height $H_1$ dimension is about 18 mm. In a further embodiment the height $H_1$ dimension is greater than about 12 mm and less than about 24 mm.

Similarly, each wax melt 104 includes a length dimension $L_1$ (see FIG. 4) as measured along the upper or lower surface (e.g., 124 or 126) between opposing sidewalls 122a, 122c. In one embodiment, the length dimension $L_1$ is between about 20 mm to about 40 mm, and in another embodiment is between about 25 mm to about 35 mm. In another embodiment, the length dimension $L_1$ is about 30 mm. In a further embodiment the length dimension $L_1$ is greater than about 26 mm and less than about 32 mm. Additionally, each wax melt 104 includes a width dimension $W_1$ (see FIG. 4) as measured along the upper or lower surface (e.g., 124 or 126) between opposing sidewalls 122b, 122d. In one embodiment, the width dimension $W_1$ is between about 20 mm to about 40 mm, and in another embodiment is between about 25 mm to about 35 mm. In another embodiment, the width dimension $W_1$ is about 30 mm. In a further embodiment the width dimension $W_1$ is substantially the same as the length dimension $L_1$.

Each wax melt 104 is also defined by the weight thereof. In particular, each wax melt 104 is sized with respect to the warmer 102 to emit a volatile for a specific pre-defined time period. To accomplish this emission, each wax melt 104 weighs between about 0.005 kg to about 0.04 kg. In one embodiment, each wax melt 104 weighs more than about 0.01 kg and less than about 0.03 kg. In another embodiment, each wax melt 104 weighs more than about 0.01 kg. In an additional embodiment, each wax melt 104 is about 0.02 kg.

The wax melts 104 are each designed to carry a volatile material that is to be dispersed as the wax melt 104 liquefies on the warmer 102, although it is contemplated that the wax melt 104 could be devoid of a volatile substance in some embodiments. It should be recognized that the volatile material, if present, is emitted from the wax melt 104 at a slow rate (e.g., under about 3 mg/hr) while the wax melt 104 is at room temperature (about 23° C.). Once the wax melt 104 is exposed to a relatively low amount heat (e.g., an amount typical for a heater within a wax warmer), the wax body 120 begins to liquefy and diffusion of the volatile material increases. Therefore, heating the wax melt 104 increases diffusion of the volatile material to provide a boost or spike of fragrance (or other volatile material) to the area surrounding the wax melt 104.

Each wax melt 104 comprises a base wax, and optionally includes one or more of a fragrance, a stabilizer, a dye, and/or other components known in the candle art. In one specific embodiment, the base wax is present in an amount of about 80 wt. % to about 98 wt. %, and in another embodiment is present in an amount of about 92 wt. %. Paraffin, vegetable, and/or other types of wax may be suitable for use in the wax melt 104. One suitable wax is a paraffin wax provided under the trade name PARAFLEX 4891A, and available from the International Group, Inc. (Toronto, Canada).

The wax melt 104 may optionally include a stabilizer and/or a dye, which are known in the art and available from commercial suppliers. In one embodiment, the stabilizer is present in an amount of about 0.1 wt. % to about 1 wt. %, and in another embodiment is present in an amount of less than about 1 wt. %. In one embodiment, the dye is present in an amount of about 0.1 wt. % to about 1 wt. %, and in another embodiment is present in an amount of less than about 1 wt. %.

The wax melt 104 may further include a volatile substance, which may be present in an amount of about 2 wt. % to about 20 wt. %, and in another embodiment is present in an amount of about 6 wt. %. The volatile substance present in the wax melt 104 may be that of a fragrance or an insecticide, a deodorizing and/or a cleaning substance, or the like. The volatile substance may also comprise other actives, such as a sanitizer, an air freshener, an odor eliminator, a mold or mildew inhibitor, an insect repellent, an insecticide, and/or the like, and/or have aromatherapeutic properties. The fragrance according to this disclosure may comprise one or more fragrant materials or materials that provide chemically active vapors. In one embodiment, the fragrance can comprise and/or include volatile, fragrant compounds including, but not limited to natural botanic extracts, essences, fragrance oils, and so forth. As is known in the art, many essential oils and other natural plant derivatives contain large percentages of highly volatile scents. In this regard, numerous essential oils, essences, and scented concentrates are commonly available from companies in the fragrance and food businesses.

In one particular embodiment, the base wax is present in an amount of about 91.5 wt. %, the fragrance is present in an amount of about 6.5 wt. %, the stabilizer is present in an amount of about 1 wt. %, and the dye is present in an amount of about 1 wt. %. In another embodiment, the base wax is present in an amount of about 93 wt. %, the fragrance is present in an amount of about 6.5 wt. %, the stabilizer is present in an amount of about 0.3 wt. %, and the dye is present in an amount of up to about 0.4 wt. %.

The coloration provided to the wax melt 104 may be used to convey different properties about the wax melt 104 to the consumer. For example, the color may be associated with a particular fragrance and/or volatile contained therein (e.g., burnt orange associated with pumpkin spice fragrance). The color of the wax melt 104 may be characterized by a substantially uniform single color such as red, orange, yellow, green, blue, purple, and/or other colors. In the embodiment depicted in FIGS. 1-7, the wax melt 104 is imparted with a single color, but small discolorations (e.g., specks, etc.) may be present within the wax melt 104 that are formed during the manufacturing process. In one embodiment, the wax melt 104 is a single color.

Figure 6:
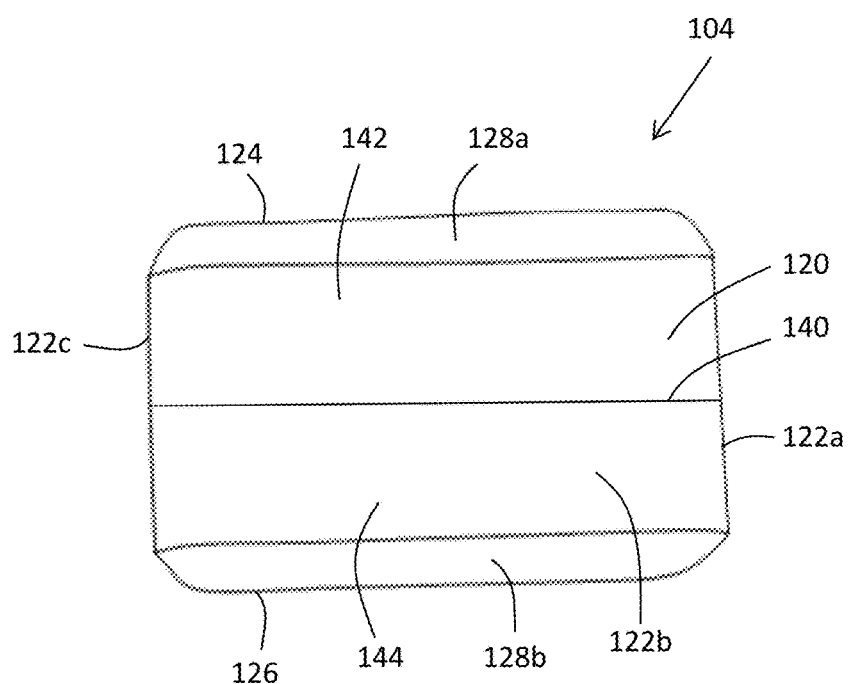
FIG. 6 is a side elevational view of another embodiment of a wax melt.

In another embodiment shown in FIG. 6, the wax melt 104 comprises two separate colors. In particular, at least a portion of the wax melt 104 above a longitudinal center axis 140 is provided with a first color 142, whereas at least a portion of the wax melt 104 below the center axis 140 is imparted with a second color 144. In a further embodiment depicted in FIG. 7, a pattern 146 may be provided to a portion of the wax melt 104. The pattern 146 may be any shape and size and, in one embodiment, comprises swirls. The pattern 146 may be characterized by at least two visually contrasting colors.

It is further contemplated that the wax melt 104 may include two fragrances that correspond to one or more portions of the wax melt 104 and/or one or more colors. For example, in one embodiment, the wax melt 104 includes the first color 142 and a first fragrance associated therewith, and the second color 144 and a second fragrance associated therewith (see FIG. 6). Numerous combinations are possible that embody the concept described herein. For example, the first color may be maroon and correspond to a cinnamon fragrance while the second color may be green and correspond to a pine tree fragrance. Similarly, the first color may be orange and correspond to a pumpkin pie fragrance while the second color may be white and correspond to vanilla. In another embodiment, the first color may be light blue and correspond to fresh linen while the second color may be light purple and correspond to lavender.

Figure 7:
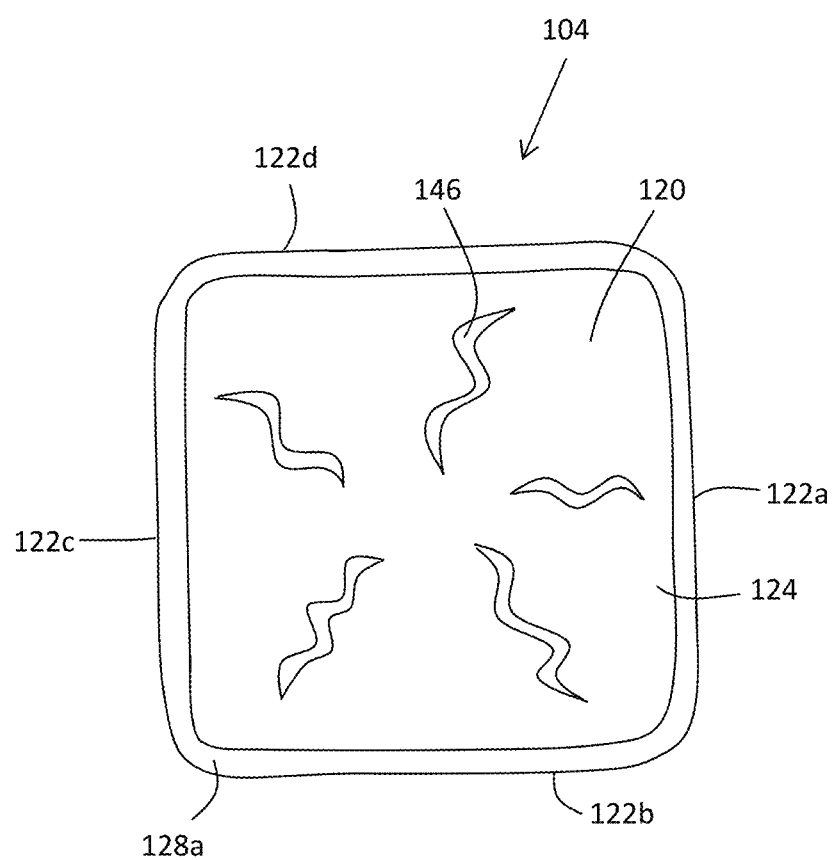
FIG. 7 is a top elevational view of a different embodiment of a wax melt.
Figure 7A:
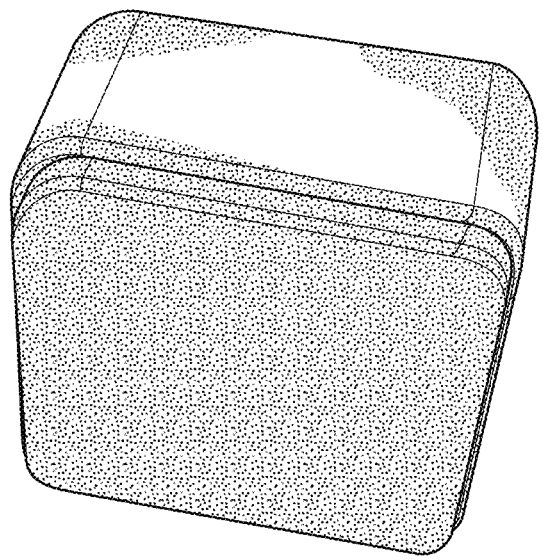
FIG. 7A is a top isometric view of a further embodiment of a wax melt.
Figure 7B:
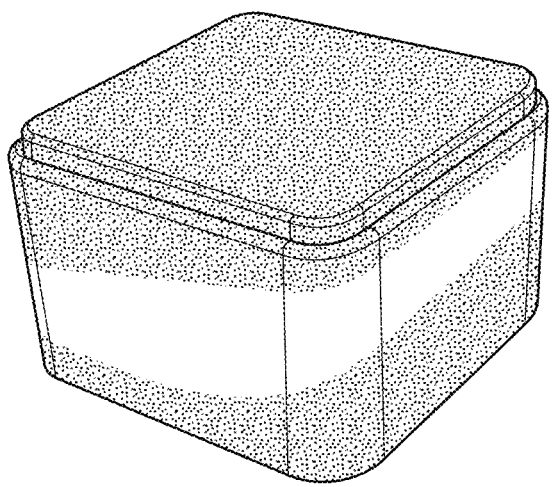
FIG. 7B is a front isometric view of a different embodiment of a wax melt.
Figure 7C:
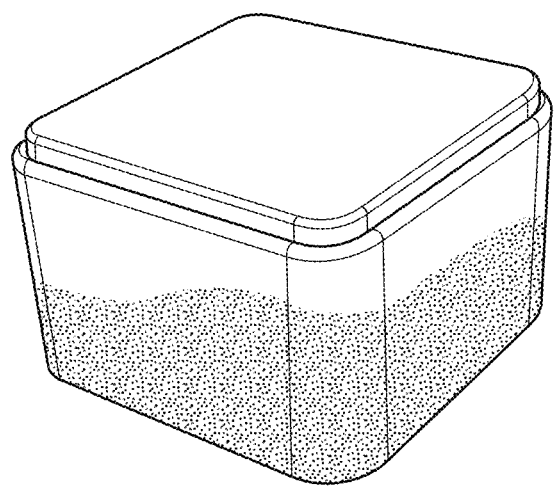
FIG. 7C is a front isometric view of yet another embodiment of a wax melt.
Figure 7D:
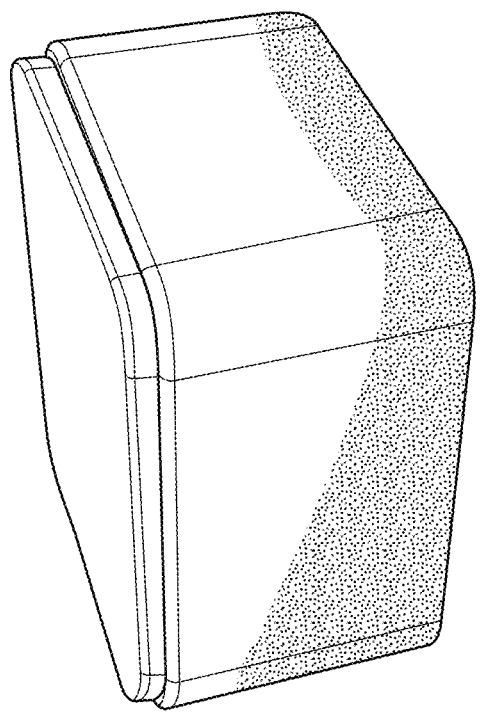
FIG. 7D is a side isometric view of a further embodiment of a wax melt.
Figure 7E:
FIG. 7E is a top isometric view of another embodiment of a wax melt.
Figure 7F:
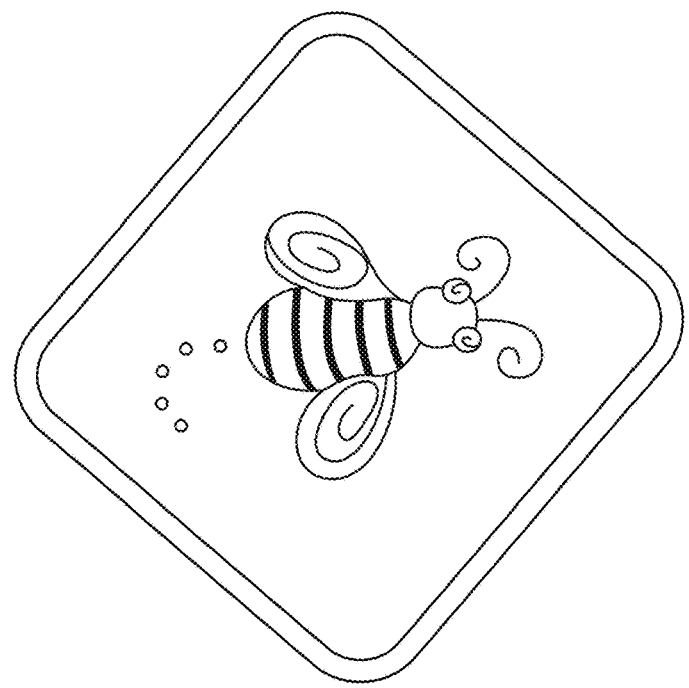
FIG. 7F is a top isometric view of a different embodiment of a wax melt.

It is envisioned that numerous color and fragrance combinations are possible and are within the scope of this disclosure. Numerous variations of the wax melt 104 consistent with this disclosure are depicted in FIGS. 7A-7F. For example, FIG. 7A depicts a wax melt 104 having a mottled appearance (i.e., uneven spots). FIG. 7B is a wax melt 104 that includes three layers that correspond to colors and/or fragrance patterns. In particular, it is contemplated that the layers disposed adjacent the top and bottom surfaces 124, 126 of the wax melt 104 are substantially the same color and the layer disposed therebetween is a different color. In a further embodiment, all three layers are defined by a different color. In still a further embodiment, the colors each correspond to a different fragrance. FIG. 7C depicts a wax melt 104 having a tie dyed appearance. FIG. 7D shows a wax melt 104 having two layers that are angled with respect to each other. The angled layers each correspond to a color that is different from each other. FIGS. 7E and 7F depict wax melts 104 that include a pattern. In the embodiment shown in FIG. 7E the pattern is embossed into the surface of the wax melt 104. In the embodiment shown in FIG. 7F, the pattern is applied to the surface of the wax melt 104 using ink or other coloration techniques. In some embodiments, the pattern may be embossed into the surface and/or protruding from the surface of the wax melt 104. The pattern may be embossed and/or imparted to the wax melt 104 during formation, or may be applied to the wax melt 104 during a separate step. In one embodiment, the embossed pattern may further be applied in a contrasting color to that of the underlying wax melt 104 for better visual clarity (e.g., using a color that is different from the wax melt 104). In another embodiment, the embossed pattern is applied to the wax melt 104 and is not imparted with a different color.

In some embodiments, the wax melt 104 includes different combinations of fragrances to enhance the user's experience during melting. For example, in a wax melt 104 that comprises three layers, one layer (e.g., the middle layer) may include a separate fragrance and/or additive that provides a boost of fragrance to the user before the next layer of the wax melt 104 liquefies. This boost may be accomplished using a fragrance additive, using a fragrance that is different from the fragrance disposed in other layers of the wax melt 104, and/or providing the fragrance in a higher amount than that of the surrounding layer(s).

In some embodiments, the fragrance combination used in the wax melt 104 is designed to provide a user experience that is associated with a holiday, a feeling, a season, and/or other experiences. For example, a wax melt 104 may impart the experience and/or feeling of a holiday meal or flavors. In particular, the combination of pumpkin, vanilla, and coffee may be used to invoke a fall fragrancing experience. Another combination may include a clean linen fragrance associated with a white layer, a dark blue layer imparted with a higher intensity clean soapy fragrance, and a light yellow layer with a light citrus fragrance to invoke a sunny day. In a further example, a cocoa fragrance is associated with a brown layer, a peppermint fragrance is associated with a pink or red layer, and a marshmallow fragrance is associated with a white layer. Other fragrance and/or color combinations are contemplated that include a soapy fragrance provided in a dark blue color layer in combination with a lavender fragrance provided in a lavender color layer. In another embodiment, the wax melt 104 includes an apple cinnamon fragrance provided in a dark red or maroon layer in combination with a vanilla fragrance that is provided in a white or off-white layer. In a further embodiment, the wax melt 104 includes one or more floral fragrances such as a rose fragrance provided in a light yellow layer in combination with a lavender peach blossom fragrance that is provided in a purple layer. In still a different embodiment, the wax melt 104 includes a woody fragrance (e.g., Cashmere woods) provided in a brown layer in combination with a vanilla fragrance that is provided in a white or off-white layer. It should be noted that the specific colors associated with each of the fragrances are examples and that other fragrance/color combinations may be used.

The wax melts 104 are designed to emit one or more volatile materials or otherwise liquefy for a specific time period that provides the user with certainty about the longevity of the release of the volatile material. For example, in one embodiment, a single wax melt 104 liquefies completely in the reservoir 110 with heat applied to the wax melt 104 by the heater of the warmer 102 at a temperature of about 75° C. after a time period of between about 30 minutes to about 80 minutes using the warmer 102 disposed in a room having a temperature of about 21° C. In another embodiment, a single wax melt 104 liquefies completely over a time period of about 60 minutes using the warmer 102 disclosed herein with heat applied to the wax melt 104 by the heater of the warmer 102 at a temperature of about 75° C. disposed in a room at about 21° C. In a further embodiment, a single wax melt 104 liquefies completely with heat applied to the wax melt 104 by the heater of the warmer 102 at a temperature of about 75° C. over a time period of between about 50 minutes to about 70 minutes using the warmer 102 disclosed herein disposed in a room at about 21° C. In still a further embodiment, a single wax melt 104 liquefies completely with heat applied to the wax melt 104 by the heater of the warmer 102 at a temperature of about 75° C. over a time period of greater than about 30 minutes using the warmer 102 disclosed herein disposed in a room at about 21° C.

The wax melts 104 are further designed to liquefy at a specified temperature that is related to the heating capabilities of the warmer 102. For example, the wax melts 104 are each designed to melt at a temperature of between 40° C. to about 90° C. In another embodiment, the wax melts 104 are each designed to melt at a temperature of between about 50° C. to about 85° C. The melting and/or physical properties of the wax melts 104 provide specific diffusion capabilities according to the strength of the wax warmer 102, but also provide stability to the wax body 120 such that the wax melts 104 do not liquefy while being transported and/or are being handled prior to use.

One unique characteristic of the wax melts 104 disclosed herein is the substantially non-greasy feel when the wax melts 104 are being handled. The greasy feel of the wax melts 104 may be characterized by the oil content therein that is present without the addition of fragrance oil. In one embodiment, the oil content of a wax melt 104 is between about 0.5% to about 5%, as determined using ASTM method D721 after the wax melts 104 have been blended and pressed. In other embodiments, the oil content of a wax melt 104 is between about 0.5% to about 5.0%. In a different embodiment, the oil content of a wax melt 104 is less than about 1.0%. In a particular embodiment, the oil content of the wax melt 104 (excluding fragrance oil) is about 0.5%.

The wax melts 104 are formed using a manufacturing process whereby wax prills are formed and then pressed together to form the wax body 120. The wax prills may be formed by melting a wax composition in a vessel and adding one or more of the desired volatile materials, coloring agents, UV stabilizers, and other optional materials. During this process, the additives become entrained into the particulate as the wax is being mixed. After mixing, the molten wax is sprayed through a nozzle into a cooling chamber. The dispersed wax particulate solidifies due to the cooler air within the cooling chamber. As the particulate solidifies, prilled wax particles are formed, which generally have the appearance of a sphere, flake, or the like and typically have a diameter dimension of less than about 2 mm. After the wax prills are formed, the prills are pressed together and introduced into a compression mold to form a wax melt 104 having a compressed core comprising prilled wax particles. The pressed wax melt 104 is provided with substantially planar surfaces 124, 126 as discussed herein that may include a plurality of interstices formed between one or more prilled wax particles. Optionally, the wax melt 104 may be imparted with a pattern, stamped, printed, and/or embossed as discussed previously herein. After being formed 104, the wax melts 104 are added to the container 106, as described in more detail hereinbelow.

Figure 8:
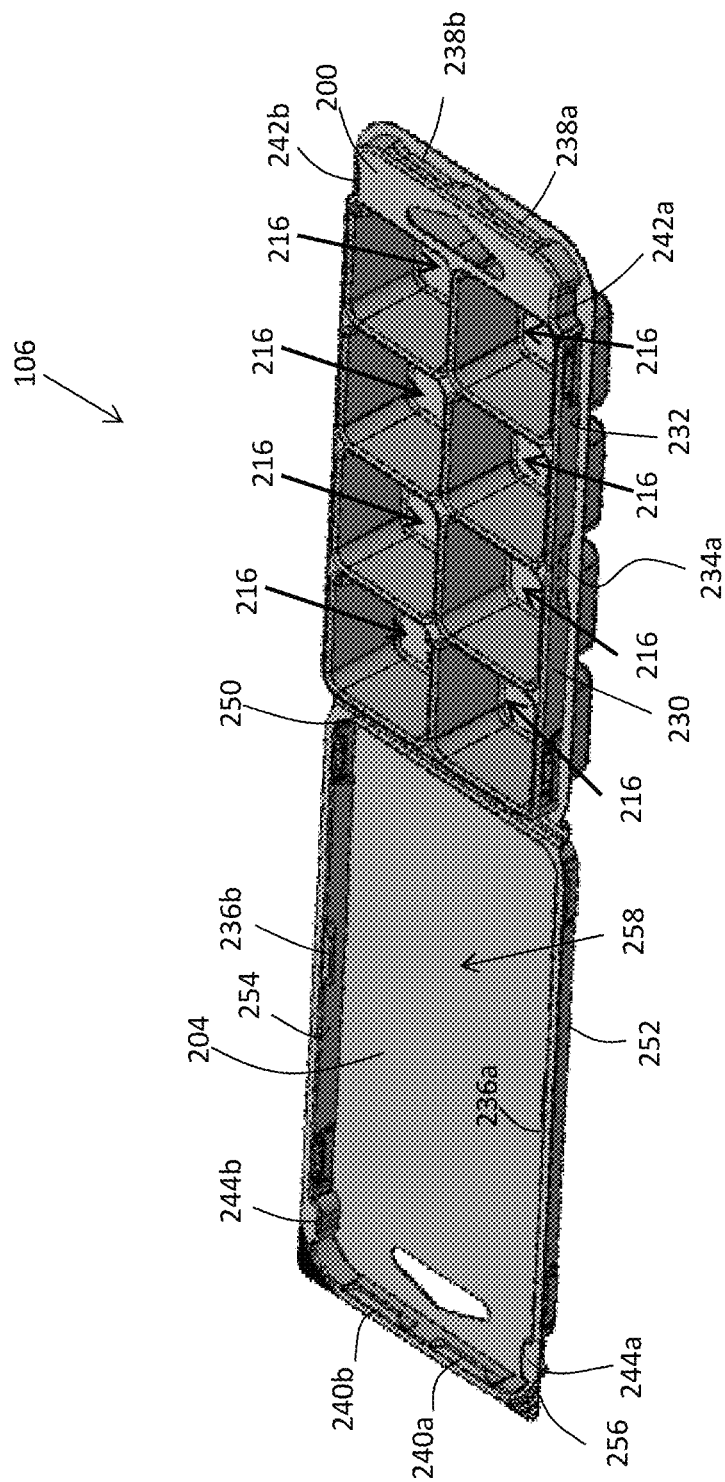
FIG. 8 is an isometric view of a container similar to the one shown in FIG. 2 including a lid in an open position.
Figure 9:
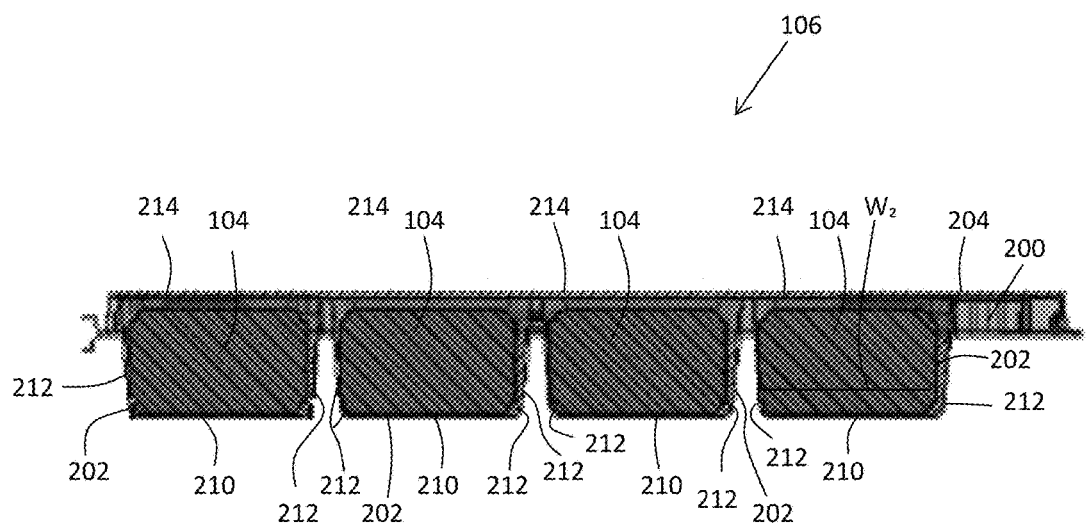
FIG. 9 is a partial cross-sectional view of the container of FIG. 8 taken along the line 9-9 of FIG. 10.
Figure 10:
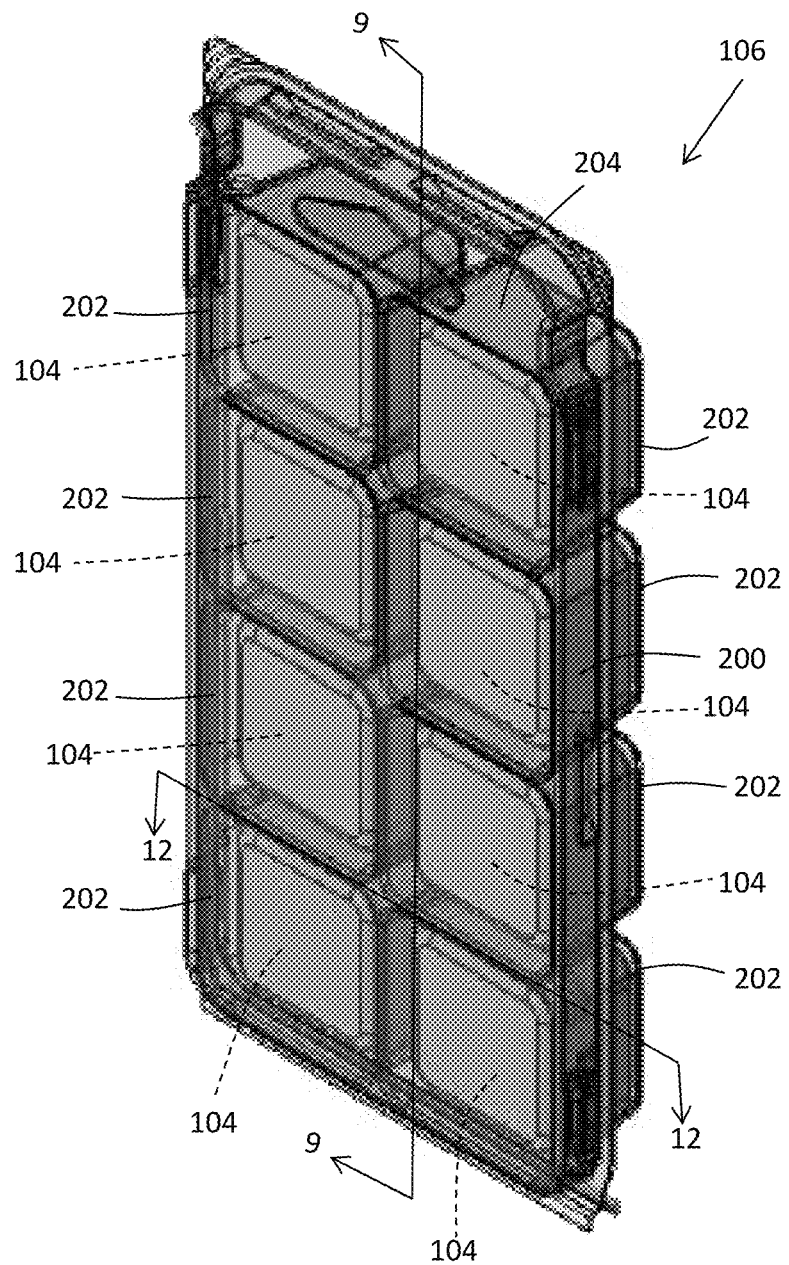
FIG. 10 is a front isometric view of the container of FIG. 8 with wax melts disposed therein and the lid in a closed position.

Now turning to FIGS. 8-12, the container 106 is designed to hold a plurality of wax melts 104 (see FIGS. 2 and 10). The container 106 includes a substantially rectangular body 200 having a plurality of discrete receptacles 202 therein. The body 200 further includes a lid 204 hingedly attached thereto. The container 106 preferably includes a receptacle 202 for each wax melt 104 such that each of the wax melts 104 are retained and spaced from each other so that they are not in contact with one another.

Figure 12:
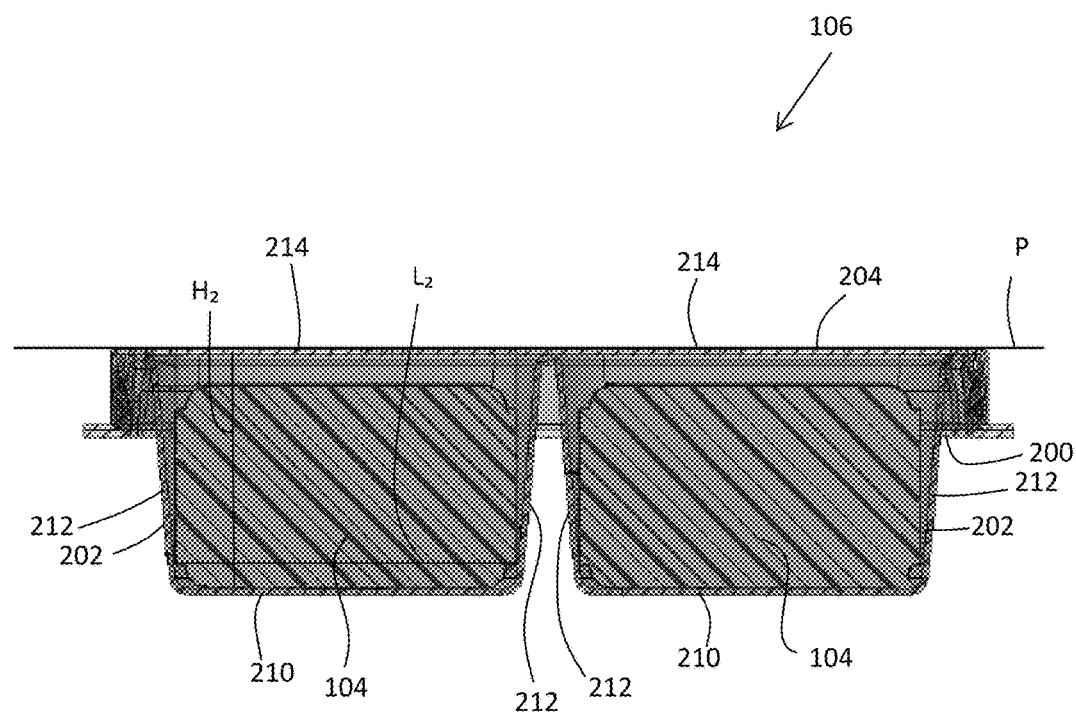
FIG. 12 is a partial cross-sectional view of the container of FIG. 8 taken along the line 12-12 of FIG. 10.

As best seen in FIGS. 9 and 12, each receptacle 202 is defined by a substantially horizontal base 210 having four slightly angled sidewalls 212 protruding upwardly and outwardly therefrom that terminate at upper edges 214. The base 210 and sidewalls 212 collectively form an opening 216 (see FIG. 8) that is designed to accommodate a single wax melt 104. The sidewalls 212 are imparted with a slightly rounded curvature at intersecting corners to correspond to the curvature of the wax melt 104.

Each receptacle 202 includes a height dimension $H_2$ (see FIG. 12) as measured along the sidewall 212 from the horizontal base 210 to the upper edge 214. In one embodiment, the height dimension $H_2$ is between about 16 mm to about 24 mm. In another embodiment, the height dimension $H_2$ is about 20 mm. In a further embodiment the height dimension $H_2$ is slightly greater than the height dimension $H_1$ of the wax melt 104. In one specific embodiment, the height dimension $H_2$ is within about 2 mm of the height dimension $H_1$ of the wax melt 104.

Similarly, each receptacle 202 includes a length dimension $L_2$ (see FIG. 12) as measured along one sidewall 212 between opposing ends thereof adjacent to the base 210. In one embodiment, the length dimension $L_2$ is between about 28 mm to about 34 mm. In another embodiment, the length dimension $L_2$ is about 31 mm. In a further embodiment the length dimension $L_2$ is slightly greater than the length dimension $L_1$ of the wax melt 104. In one specific embodiment, the length dimension $L_2$ is within about 2 mm of the length dimension $L_1$ of the wax melt 104. Each receptacle 202 also includes a width dimension $W_2$ (see FIG. 9) as measured along the adjacent sidewall 212 between opposing ends thereof adjacent to the base 210. In one embodiment, the width dimension $W_2$ is between about 28 mm to about 34 mm. In another embodiment, the width dimension $W_2$ is about 31 mm. In a further embodiment, the width dimension $W_2$ is substantially equal to the length dimension $L_2$.

When the wax melt 104 is placed into the receptacle 202, a gap 220 (see FIG. 2) is formed around the perimeter thereof between the sidewalls 122a-122d of the wax melt 104 and the sidewalls 212 of the receptacle 202. In one embodiment, none of the sidewalls 122a-122d of the wax melt 104 are in contact with any of the sidewalls 212 of the receptacle 202 when the container 106 is being supported on a substantially level horizontal surface. In another embodiment, the wax melts 104 are positioned within the receptacles 202 such that the upper surface 124 of each of the wax melts 104 is positioned below a plane P (see FIG. 12) defined by the upper edges 214. In a further embodiment, each wax melt 104 is discretely contained within a corresponding receptacle 202.

Figure 11:
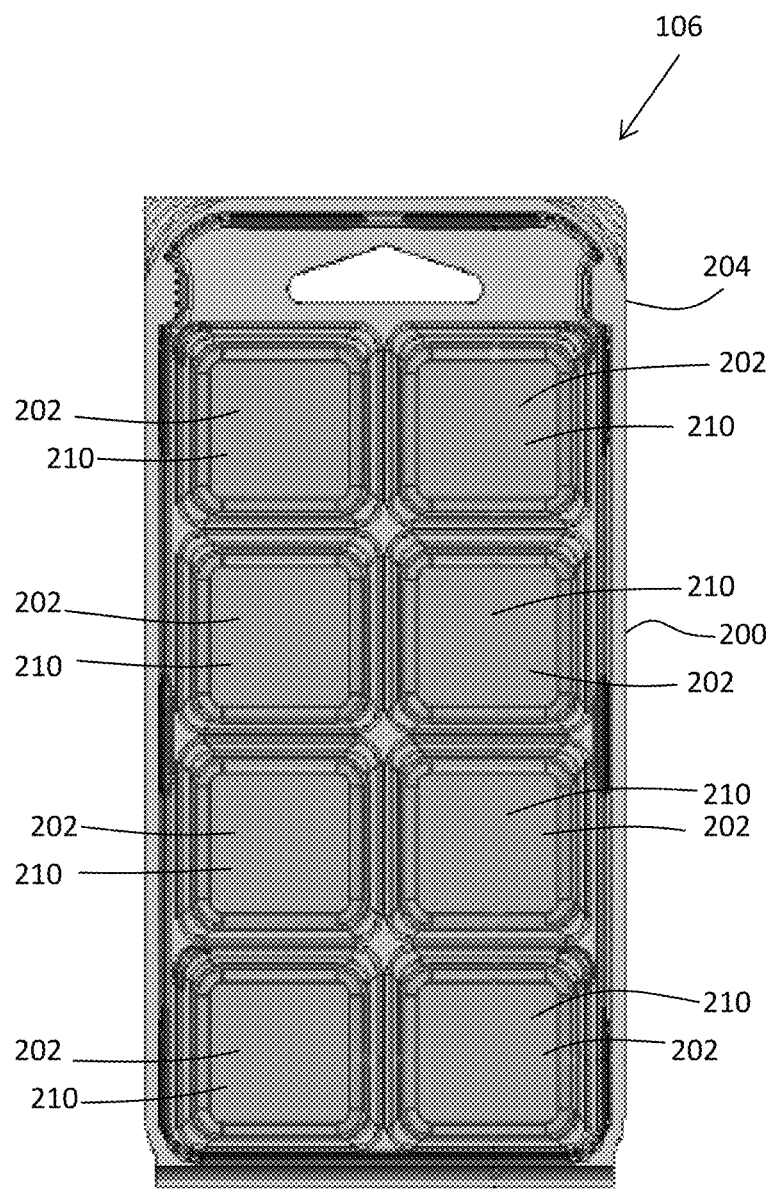
FIG. 11 is a bottom elevational view of the container of FIG. 8.
Figure 13:
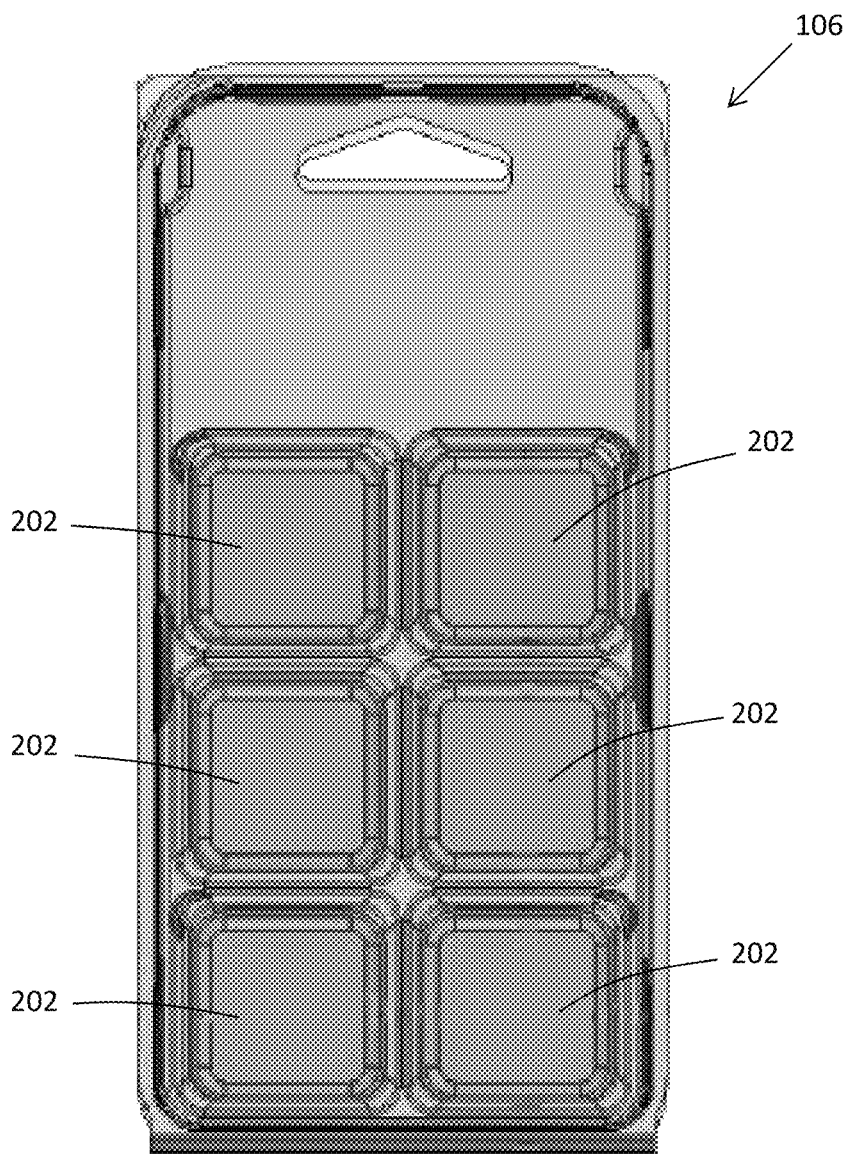
FIG. 13 is a bottom elevational view of another embodiment of a container

As shown in FIG. 11, the container 106 includes eight receptacles 202 aligned in a two by four pattern. In another embodiment shown in FIG. 13, the container 106 includes six receptacles 202 aligned in a two by three pattern. In still a different embodiment, the container 106 includes three receptacles 202 aligned in a three by one pattern. In a different embodiment, the container 106 includes two receptacles 202 aligned in a two by one pattern. In yet another embodiment, the container 106 includes four receptacles 202 aligned in a two by two pattern. In a further embodiment, the container 106 includes eleven receptacles 202.

It is further contemplated that the container 106 may include wax melts 104 imparted with the same color and/or fragrance (or other volatile material). In another embodiment, the container 106 may include a plurality of wax melts 104 having different color and/or fragrance combinations. For example, the container 104 may include four wax melts 104 that correspond to a first scent and four wax melts 104 that correspond to a second scent. It is envisioned that numerous color and fragrance combinations may be included within the container 106, e.g., as pairs of fragrances, triplets of wax melts 104 in the two by three pattern, and as a variety pack that may include a different fragrance in each receptacle 216. Wax melts 104 having a single fragrance may be contained with wax melts 104 that contain more than one fragrance. For example, single scent spruce fragrance wax melts 104 may be packaged with apple cinnamon fragrance wax melts 104 and/or with one or more wax melts 104 having an apple cinnamon fragrance in one layer and a vanilla fragrance associated with a second layer. In a different embodiment, six wax melts 104 may be packaged together to include two wax melts 104 having a pumpkin spice fragrance, two wax melts 104 having an apple cinnamon fragrance, and two wax melts 104 having an outdoors or woody (e.g., Cashmere Woods) fragrance.

Returning again to FIG. 8, the body 200 of the container 106 includes a sidewall 230 circumscribing the perimeter thereof that extends about exterior edges of each of the receptacles 202 and terminates at an outwardly extending flange 232. The flange 232 is substantially flat and is designed to accommodate portions of the lid 204.

The container 106 includes a locking mechanism to releasably attach the lid 204 thereto. In particular, the sidewall 230 includes two centrally disposed elongate notches 234a, 234b on opposing sides thereof that are designed to interact with corresponding protrusions 236a, 236b on the lid 204. Similarly, two additional elongate notches 238a, 238b are disposed at ends of the container 106 and are designed to interact with corresponding protrusions 240a, 240b on the lid 204. Two rounded cutouts 242a, 242b are disposed between the notches 234a, 234b, 238a, 238b and are designed to accommodate rounded protrusions 244a, 244b disposed on the lid 204. The notches 234a, 234b, 238a, 238b, and the cutouts 242a, 242b define a portion of the locking mechanism disposed on the body 200 of the container 106. Although numerous notches and/or protrusions are depicted in specific locations, it is envisioned that any number of notches and/or protrusions could be included in various locations on the container 106 that still allows the lid 204 to releasably attach thereto.

Still referring to FIG. 8, the lid 204 is attached to the container 106 via a hinge 250. The lid 204 includes a base 252 with four sidewalls 254 extending therefrom. The sidewalls 254 terminate at an outwardly extending flange 256 that circumscribes the perimeter of the lid 204. The base 252 and sidewalls 254 collectively define a substantially shallow compartment 258. Protrusions 236a, 236b, 240a, 240b, 244a, 244b all extend inwardly from the flange 256 into the compartment 258.

To close the lid 204 of the container 106, the lid 204 may be rotated about the hinge 250 until protrusions 236a, 236b, 240a, 240b, 244a, 244b contact and interact with notches 234a, 234b, 238a, 238b, and cutouts 242a, 242b, respectively. After rotation, force is applied to the lid 204 to allow the notches and cutouts to ride over the sidewall 230 and into snap-fit connection with the protrusions. To open the lid 204, the process is reversed. In other embodiments, the lid 204 may be releasably attached to the container 106 in other manners. For example, the lid 204 may be releasably attached using an interference fit, adhesive, and the like.

The container 106 is preferably manufactured from a material that supports the wax melts 104, minimizes melting of the wax melts 104, and allows the wax melts 104 to be easily removed therefrom. In particular, the wax melts 104 should be able to be removed from the container 106 without crumbling and without having to break the wax melt 104. Materials that facilitate the aforementioned properties include a polymer such as polyethylene terephtalate (PET), and more specifically virgin PET, recycled PET, and/or combinations thereof. Additionally, the materials may include combinations of manufactured, natural, and/or recycled or reclaimed materials.

After manufacturing, the wax melts 104 are placed into the receptacles 202 of the container 106. The wax melts 104 are easily removed from the container 106, which is one advantage over the prior art. Numerous factors are relevant with respect to this aspect. For example, some factors include the oil content of the wax melts 104, the material used to manufacture the container 106, the manufacturing method of the wax melts 104 (i.e., prilled and pressed as opposed to poured), and the surface energy and/or adhesion properties of the wax melts 104 and the container 106. In one embodiment, the receptacles 202 have a low surface energy such that the wax melts 104 do not substantially stick thereto. In a further embodiment, the surface energy is such that the wax melts 104 easily slide out of the receptacles 202 when the container 106 is flipped over and the lid 204 is in the open position (e.g., without any user assistance).

Figure 14:
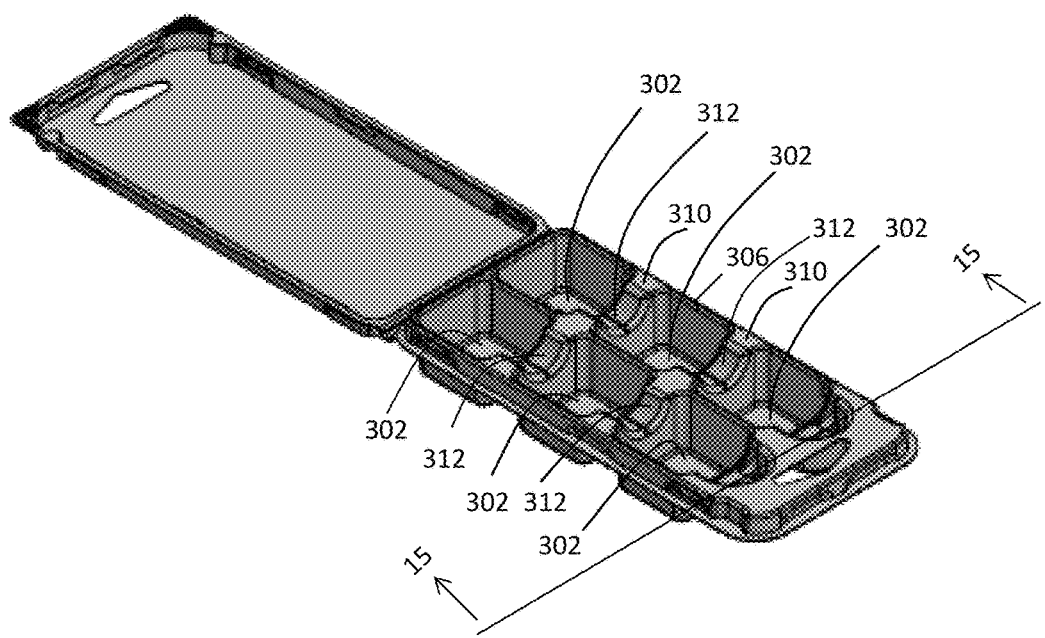
FIG. 14 is a front isometric view of a different embodiment of a container.
Figure 15:
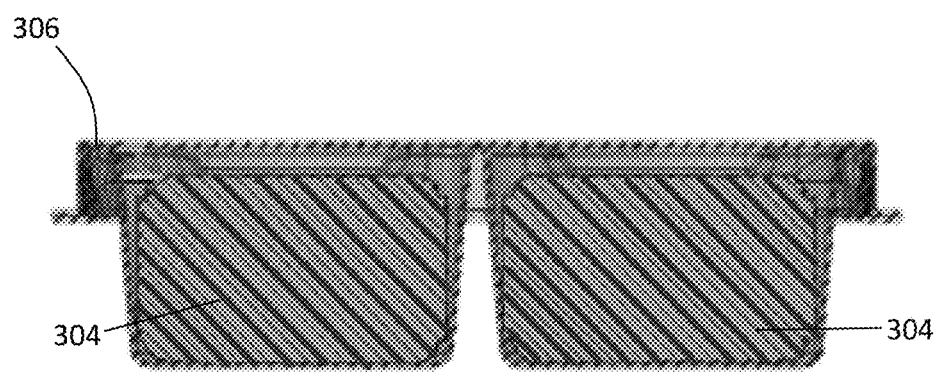
FIG. 15 is a cross-sectional view of the container of FIG. 14 taken generally along the line 15-15 of FIG. 14 further including wax melts.
Figure 16:
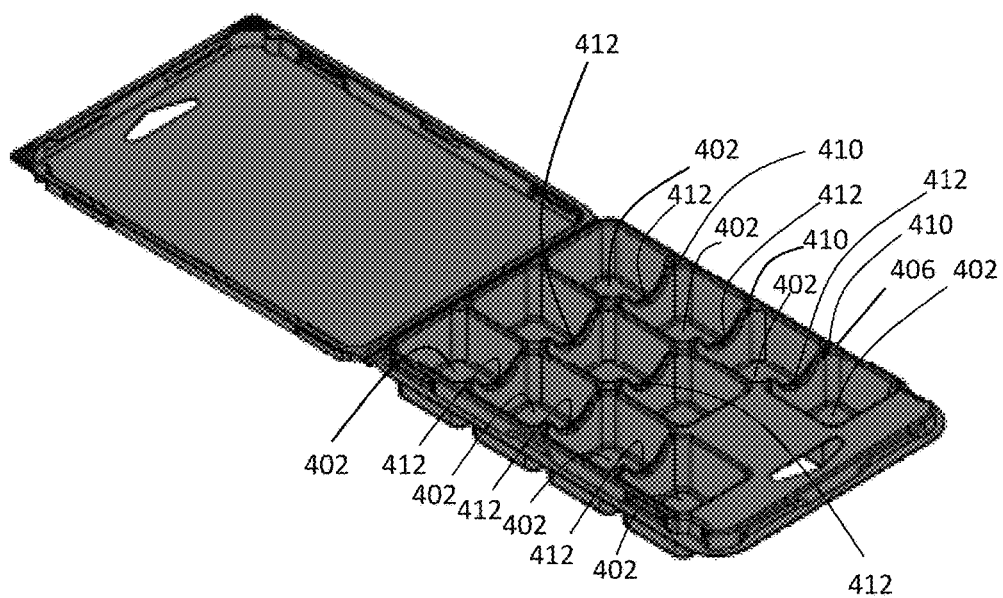
FIG. 16 is a front isometric view of a further embodiment of a container.

Another embodiment of a container 306 is depicted in FIGS. 14 and 15. The container 306 is similar to the container 106 except for the differences noted herein. The container 306 includes a plurality of adjacent receptacles 302 configured to hold one or more wax melts 304 (see FIG. 15). A sidewall 310 is provided between at least some of the receptacles 302 and is interrupted by one or more curved surfaces 312. Each curved surface 312 provides clearance for a user's finger when the user is removing the wax melt 304 from the container 306. In this embodiment, the wax melt 304 protrudes upwardly above the curved surface 312. In some instances, the user may position two fingers (i.e., index finger and thumb) on adjacent curved surfaces 312 on opposing sides of the wax melt 304. After positioning the fingers, the user squeezes inwardly to grasp the wax melt 304. The curved surfaces 312 are sized to allow at least a portion of an average size human finger to be disposed adjacent thereto. One or more curved surfaces 312 may be imparted to different parts of the container 306 to facilitate wax melt 304 removal therefrom. Although depicted as curved, the surfaces 312 may be any shape and size consistent with the purpose disclosed herein. A further embodiment of a container 406 is shown in FIG. 16. The container 406 is similar to containers 106, 306, except the container 406 includes eleven receptacles 402 having sidewalls 410 interrupted by curved surfaces 412.

A method of providing one or more of the components of the wax melt system 100 comprising the wax melts 104, container 106, and/or wax warmer 102 is contemplated. For example, the wax melts 104 may be provided in the container 106 with or without the wax warmer 102. Once a consumer purchases the wax melt system 100, the wax warmer 102 is removed from the packaging and turned on (e.g., via plug, battery, tea light, and the like). The lid 204 of the container 106 is opened and the consumer is able to select a wax melt 104. The wax melt 104 may be grasped and removed from the container 106 by placing one or more fingers in the space 220 between the wax melt 104 and the receptacle 202. In another embodiment, the container 106 may be tilted or otherwise rotated until a wax melt 104 slides out of the receptacle 202. In a further embodiment, the container 106 may be imparted with divots or other curvature (see e.g., FIGS. 14-16) to allow a user to more easily insert a finger into the receptacle 202 to grasp the wax melt 104.

At this point, the wax melt 104 is placed on the reservoir 110 of the wax warmer 102 with either the upper surface 124 or the lower surface 126 of the wax melt 104 contacting the surface of the reservoir 110. The wax melt 104 is designed to be centrally disposed and spaced away from (i.e., does not touch) the raised edge that circumscribes the reservoir 110. As the temperature of the reservoir 110 is increased, the wax melt 104 begins to liquefy and the volatile material is released therefrom. As the wax melt 104 liquefies, diffusion of the volatile material increases to greater than about 3 mg/hr.

In another embodiment, the container 106 is provided with one or more wax melts 104 having two fragrances or more that correspond to two or more colors (see e.g., FIG. 6, first color 142 associated with a first fragrance and second color 144 associated with a second fragrance). After removing the wax melt 104 from the packaging, the consumer is able to decide which fragrance will be emitted first of the two outer fragrances (if more than 1 fragrance is imparted to the wax melt 104). For example, the consumer may choose to place the wax melt 104 into the reservoir 110 of the wax warmer 102 with the second color disposed adjacent the surface of the reservoir 110. The second fragrance is released at a higher rate than the first fragrance until the wax melt 104 liquefies enough such that the first color portion of the wax melt 104 is adjacent to the molten wax pool or reservoir 110. Once the first color portion of the wax melt 104 is adjacent the surface of the reservoir 110, the diffusion rate of the first fragrance increases. In this way, the consumer is able to control which scent is to be released first and/or the intensity profile of the two fragrances over a period of time.

It is envisioned that any of the wax melts disclosed herein may be used in any of the containers disclosed herein. It is further envisioned that the containers may include any number of reservoirs suitable to hold the wax melts. In some embodiments, a first wax melt having a profile defined by one or more specific color(s), fragrance(s), number of layer(s), inclusion of other volatiles, and/or any other characteristics described herein may be provided in a container with a different wax melt having a second, different profile. The profile may be defined by any of the characteristics described herein. The second wax melt may differ from the first wax melt in any number of respects. For example, the second wax melt may be different from the first wax melt in that at least one of the color(s), fragrance(s), number of layer(s), and/or volatiles is different from that of the first wax melt. In a further embodiment, a third wax melt having a different profile from that of the first and second wax melt is provided in the same container. A fourth, fifth, and sixth wax melt, each one having a different profile of that of the first, second, and third wax melt profiles (and each other) may also be provided in a single container. It is envisioned that any number of wax melts may be provided in a single container having the same profile, different profiles, and/or combinations thereof.

In some specific embodiments, the wax melts may be provided in the containers in a uniform manner such that the wax melts are imparted with a single fragrance and/or are represented by a single color. In one specific embodiment, six wax melts may be provided in a six pack, whereby each of the wax melts is different in either look or with respect to fragrance as compared to the other wax melts. In other embodiments, the wax melts provided in the containers disclosed herein may include two or more fragrances, two or more layers, and/or two or more colors. In a further embodiment, any of the aforementioned wax melts may be provided in a container in a variety pack (e.g., at least one fragrance wax melt provided in conjunction with at least one wax melt having two or more fragrances). In other embodiments, one of more of the wax melts disclosed herein may be provided in a single container in conjunction with one or more of any of the other wax melts disclosed herein.

The containers disclosed herein may also be provided in a stacked configuration (not shown). The previously discussed design of the containers facilitate stacking such that the containers may be retained in an upright and substantially secure manner with respect to each other when the containers are being supported on a horizontal surface. In some embodiments, the containers are retained in a substantially upright manner with respect to each other when one container is stacked on the lid of an adjacent container. In one specific embodiment, a box may be provided that includes a plurality of stacked containers. The stacked containers may be configured in a manner to provide six containers disposed adjacent to, and on top of, six other containers forming a twelve pack configuration. In a further embodiment, six additional containers may be stacked on top of the twelve pack configuration to form an eighteen pack tray. In some embodiments, two or more containers may be provided in a stacked formation, whereby the containers each have the same number of reservoirs. In a different embodiment, two or more containers may be provided in a stacked formation, whereby the containers are provided with a different number of reservoirs with respect to each other. Any container with any number of reservoirs may be provided in a stacked configuration with any other container disclosed herein. Any number of containers may be provided in a stacked form to facilitate shipping of the containers after the manufacturing process. In a further embodiment, the containers may be optionally stacked on a horizontal surface and shipped without a box.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of manufacture comprising the steps of:
providing a first solid wickless wax melt and a second solid wickless wax melt, each being discrete with respect to each other and each having a body defined by two opposing substantially planar surfaces and a sidewall;
providing a container having discrete receptacles;
disposing the first solid wax melt into a first discrete receptacle of the container; and
disposing the second solid wax melt into a second discrete receptacle of the container.

2. The method of claim 1, wherein the first and second solid wax melts comprise wax prills.

3. The method of claim 1, wherein the method additionally comprises the steps of:
forming solid wax prills; and
compressing the solid wax prills into a first solid wickless wax melt and a second solid wickless wax melt.

4. The method of claim 1, wherein the first wax melt is imparted with a first fragrance and the second wax melt is imparted with a second fragrance.

5. The method of claim 1, wherein the container is provided with a lid hingedly attached thereto and a locking mechanism to facilitate closure thereof.

6. The method of claim 5, additionally comprising the step of:
closing the lid of the container after the first and second solid wax melts have been disposed therein.

7. The method of claim 1, wherein an air gap is provided between the sidewall of the first and second solid wax melts and interior sidewalls of the discrete first and second receptacles, respectively.

8. The method of claim 1, wherein the body of the first and second wax melts comprises at least three sidewalls.

9. The method of claim 1, wherein the body of the first and second wax melts comprises at least four sidewalls.

* * * * *